(12) United States Patent
Fukuda

(10) Patent No.: US 7,078,390 B1
(45) Date of Patent: Jul. 18, 2006

(54) RIBOZYMES TO GROWTH FACTOR ORIGINATING IN HUMAN PLATELET

(75) Inventor: Noboru Fukuda, Tokyo (JP)

(73) Assignee: Gentier Biosystems Incorporated, Tokyo (JP)

( * ) Notice: Subject to any disclaimer, the term of this patent is extended or adjusted under 35 U.S.C. 154(b) by 839 days.

(21) Appl. No.: 10/110,274

(22) PCT Filed: Oct. 13, 2000

(86) PCT No.: PCT/JP00/07129

§ 371 (c)(1),
(2), (4) Date: Apr. 10, 2002

(87) PCT Pub. No.: WO01/27264

PCT Pub. Date: Apr. 19, 2001

(30) Foreign Application Priority Data

Oct. 15, 1999 (JP) ................................. 11293823

(51) Int. Cl.
*C07H 21/04* (2006.01)
*C12N 5/00* (2006.01)
*A61K 31/70* (2006.01)

(52) U.S. Cl. ..................... 514/44; 536/24.1; 536/24.5; 536/23.1; 435/6; 435/375; 435/377

(58) Field of Classification Search .................... None
See application file for complete search history.

(56) References Cited

U.S. PATENT DOCUMENTS 6,770,633 B1 * 8/2004 Robbins et al. ............... 514/44

FOREIGN PATENT DOCUMENTS

| EP | 0 366 816 A1 | 5/1990 |
|---|---|---|
| WO | 92/17206 A1 | 10/1992 |
| WO | 00/43044 A1 | 7/2000 |
| WO | WO 01/30362 A2 * | 5/2001 |

OTHER PUBLICATIONS

Dorai et al., Molecular Pharmacology, vol. 46, No. 3, pp. 437-444, (1994).
Rossi et al., Pharmac. Ther., vol. 50, No. 2, pp. 245-254, (1991).
Yang et al., Biochemistry, vol. 31, No. 21, pp. 5005-5009, (1992).
Stiko-Rahm et al., Aeteriosclerosis and Thrombosis, vol. 12, No. 9, pp. 1099-1109 (1992).
Scott et al., Circulation vol. 93, No. 12, pp. 2178-2187 (1996).
Fukuda et al., American Journal of Hypertension, Ltd., vol. 10, No. 10, Part 1, pp. 1117-1124 (1997).
Fukuda, Noboru et al., Journal of Hypertension, vol. 15, No. 10, pp. 1123-1136 (1997).

* cited by examiner

*Primary Examiner*—Sean McGarry
(74) *Attorney, Agent, or Firm*—Birch, Stewart, Kolasch & Birch, LLP

(57) ABSTRACT

A ribozyme comprising the following nucleotide sequence (SEQ ID NO:14) (I):

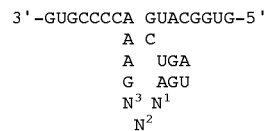

wherein A, C, G and U represent a ribonucleotide whose base component is adenine, cytosine, guanine and uracil, respectively, $N^1$ and $N^3$ are at least one pair of nucleotides capable of forming a complementary base pair with each other, and $N^2$ is at least three nucleotides capable of forming a loop.

11 Claims, 9 Drawing Sheets

FIG. 2A

```
                   ↓
5'-CACGGGG UCCAUGCCAC-3'
3'-GUGCCCCA GUACGGUG-5'
         A C
         A  U G A
         G  A G U
         C G
         A U
         G C
         G C
        C   U
         G U
```

FIG. 2B

```
                   ↓
5'-CACGGGG UCCAUGCCAC-3'
3'-GUGCCCCC GUACGGUG-5'
         A C
         A  U G A
         G  A G U
         C G
         A U
         G C
         G C
        C   U
         G U
```

*P < 0.01 vs MISMATCH RIBOZYME

*P < 0.01 vs MISMATCH RIBOZYME

US 7,078,390 B1

RIBOZYMES TO GROWTH FACTOR ORIGINATING IN HUMAN PLATELET

This application is the national phase under 35 U.S.C. § 371 of PCT International Application No. PCT/JP00/07129 which has an International filing date of Oct. 13, 2000, which designated the United States of America.

TECHNICAL FIELD

The present invention relates to a ribozyme to human platelet-derived growth factor.

BACKGROUND ART

Essential hypertension causes severe complications such as apoplexy, ischemic heart diseases and nephrosclerosis. These complications are fundamentally associated with vascular disorders by excessive proliferation of vascular smooth muscle cells (VSMC), and are the targets of the treatment of hypertension. We have already shown the enhanced expression of platelet-derived growth factor (PDGF) A-chain mRNA in spontaneous hypertensive rat (SHR)-derived VSMC (Fukuda N, Kubo A, Watanabe Y, Nakayama T, Soma M, Izumi Y, Kanmatsuse K. (1997) J. Hypertens. 15:1123., Fukuda N, Kishioka H, Satoh C, Nakayama T, Watanabe Y, Soma M, Izumi Y, Kanmatsuse K. (1997) Am. J. Hypertens. 10:1117). On the other hand, restenosis of coronary arteries takes place in about 40 percent after percutaneous transluminal coronary angioplasty (PTCA) as a treatment of myocardial infarction, and there is no effective pharmacotherapy for the restenosis at present, posing a serious problem in the field of cardiovascular diseases. Histopathologically, it is known that PDGF A-chain is involved in the migration of medial smooth muscle cells and the neointimal formation by the proliferation of (Scott N A, Cipolla G D, Ross C E, Dunn B, Martin F H, Simonet L, Wilcox J N. (1996) Circulation 93:2178).

It is thought that the cell growth can be blocked by various manners. One of them is to control the expression of growth factors including PDGF. PDGF is a potent stimulator of VSMC proliferation which displays proliferative action and migratory action to the cell growth. PDGF is a dimer protein composed of disulfide-bound polypeptides known as the A-chain and the B-chain. Three forms (AA, AB, and BB) of PDGF differ in cell distribution and biological activity, and selectively interact with at least two PDGF receptors (α and β). Stiko-Rahm et al. have shown that although cultivated VSMC or VSMC in atherosclerotic plaque expresses PDGF A-chain mRNA and secretes PDGF-AA protein, but growth-arrested normal VSMC do not express PDGF A-chain mRNA (Stiko-Rahm A, Hultgardh-Nillsson A, Regnstrom J, Hamsten A, Nilsson J. (1992) Arterioscler Thromb 12:1099).

DISCLOSURE OF THE INVENTION

It is an object of the present invention to provide gene therapeutic agents for vascular proliferative disorders. In order to evaluate how PDGF A-chain is involved in exaggerated growth of cardiovascular organs in hypertension, we have found that antisense oligodeoxynucleotide (ODN) complementary to PDGF A-chain mRNA suppresses exaggerated growth of cardiovascular organs in SHR in vitro and in vivo. This suggests the involvement of PDGF A-chain in the exaggerated growth of cardiovascular organs in hypertension. Moreover, we have found that the DNA-RNA chimera type ribozyme designed to target rat PDGF A-chain mRNA can cleave the PDGF A-chain mRNA in viable VSMC in a sequence-specific manner. As a result, it can reduce the expression of PDGF-AA protein in VSMC, and suppress the exaggerated growth of SHR-derived VSMC. Furthermore, in order to design a 38-base hammerhead ribozyme to cleave human PDGF-A chain mRNA, and to develop ribozymes for gene therapy of the vascular proliferative disorders, we examined the effect of this hammerhead ribozyme on the growth of human VSMC, and found that angiotensin II- or TGF-β-stimulated DNA synthesis in human VSMC is significantly inhibited in a dose-dependent manner, and both expressions of PDGF A-chain mRNA and PDGF-AA protein stimulated by angiotensin II in human VSMC are significantly inhibited by the ribozyme. The present invention was completed based on the above findings.

Thus, the present invention provides ribozyme which has the following base sequence (nucleotide sequence) (I)

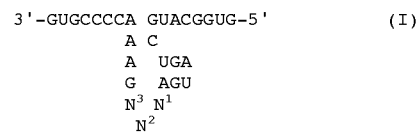

(in the sequence, A, C, G and U represent a ribonucleotide whose base component is adenine, cytosine, guanine and uracil, respectively, $N^1$ and $N^3$ are at least one pair of nucleotides capable of forming a complementary base pair with each other, and $N^2$ is at least three nucleotides capable of forming a loop)

$N^1$ and $N^3$ are preferably 1–3 pairs of nucleotides. $N^2$ is preferably 3–4 nucleotides.

Moreover, the present invention provides a ribozyme comprising the following base sequence (nucleotide sequence) (I') (SEQ ID NO: 16).

in the sequence, A, C, G and U represent a ribonucleotide whose base component is adenine, cytosine, guanine and uracil, respectively, N* contains at least two nucleotides capable of forming a complementary base pair with each other and three nucleotides capable of forming a loop.

In the sequence (I), this N* is represented by $N^1$, $N^2$, and $N^3$.

An example of the ribozyme of the present invention contain the following nucleotide sequence (II) or (II') (SEQ ID NO 1).

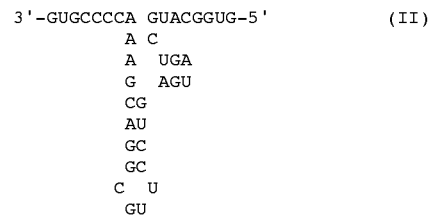

or    5'-GUGGCAUGCUGAUGAGUCCUUGCGGAC-GAAACCCCGUG-3¹ (II')

(in the sequence, A, C, G and U represent a ribonucleotide whose base component is adenine, cytosine, guanine and uracil, respectively).

Moreover, the present invention provides a complex of the above ribozyme and liposome. As the liposome, there may be illustrated a complex of N-[1-(2,3-dioleyloxy)propyl]-N,N, N-trimethylammonium chloride (DOTMA), dioleoyl phosphotidyl ethanolamine (DOPE) (for example, Lipofectin (GIBCO)) and a liner polymer mixture of ethyleneimine (for example, ExGen 500 (Euromedex)), etc.

Furthermore, the present invention provides a method of preparing the above ribozyme by chemical synthesis. As a synthetic method, the triester phosphate method, the phosphoramidite method, the phosphonate method, etc. can be used.

The present invention further provides a pharmaceutical composition comprising as an active ingredient the above ribozyme or a complex of ribozyme and a liposome. The pharmaceutical composition of the present invention is effective for preventing and/or treating vascular proliferative diseases such as hypertension, restenosis of coronary arteries after PTCA.

The present invention also provides a method of specifically cleaving target RNA using the above ribozyme.

The specific cleavage of target RNA may be performed either in vitro or in vivo. An example of target RNA is human PDGF A-chain mRNA. Moreover, the target RNA preferably contains the following nucleotide sequence (SEQ ID NO: 2):

5'-CACGGGGUCCAUGCCAC-3'

(in the sequence, A, C, G and U represent a ribonucleotide whose base component is adenine, cytosine, guanine and uracil, respectively).

BRIEF DESCRIPTION OF THE DRAWINGS

FIG. 2A (Top Sequence =SEQ ID NO:2; Bottom Sequence =SEQ ID NO:1) and FIG. 2B (Top Sequence =SEQ ID NO:2; Bottom Sequence =SEQ ID NO:13) show the sequences of a ribozyme to human PDGF A-chain mRNA and the control mismatch ribozyme. Ribozyme (lower part) can cleave PDGF A-chain mRNA after the GUC sequence (upper part), as shown by an arrow. In the mismatch ribozyme, the ribozyme sequence has undergone one base substitution from A to C at position 31 from the 5'-end.

*: $P<0.01$ compared to the mismatch ribozyme.

Figure 6:
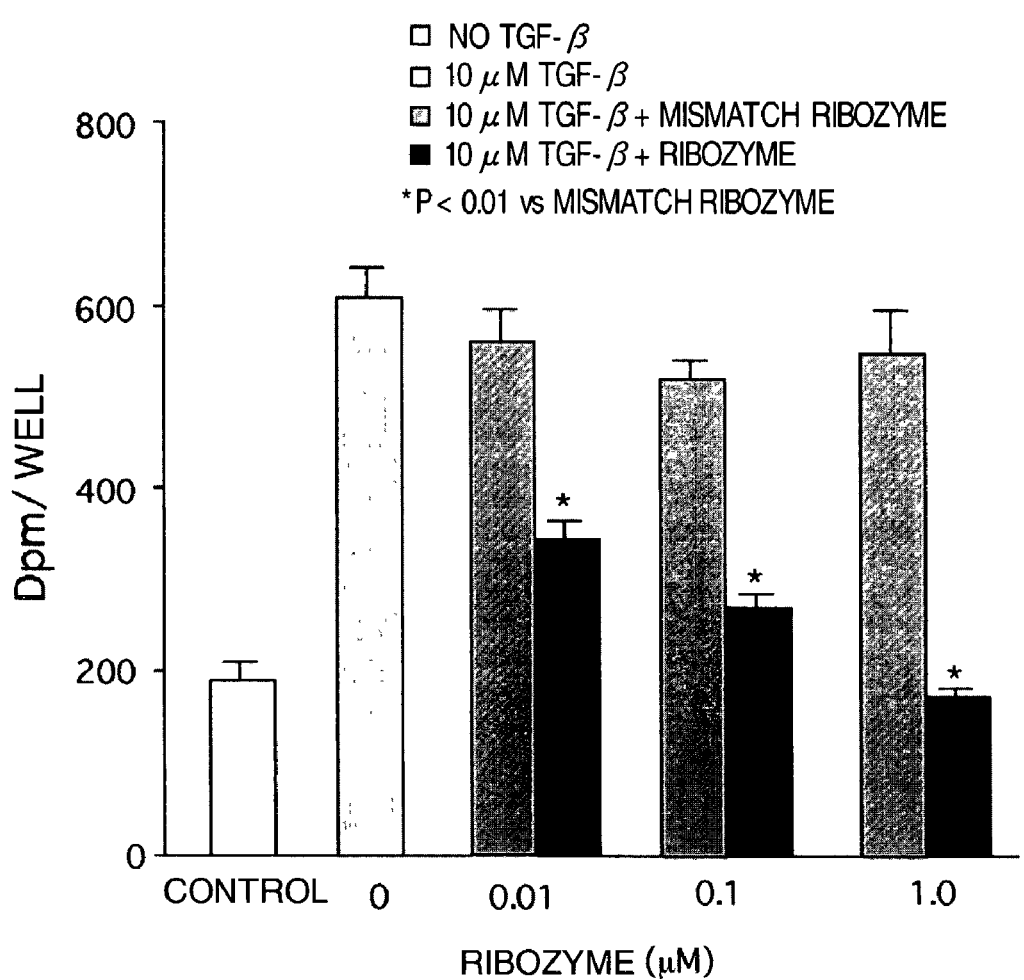

FIG. 6 shows the effect of a hammerhead ribozyme to human PDGF A-chain mRNA on TGF-β-stimulated DNA synthesis in human VSMC. The VSMC at the stationary phase was incubated together with 10 μM TGF-β and 0.01–1.0 μM ribozyme or mismatch ribozyme with Lipofectin for 20 hours. Data are expressed in mean ±SEM (n=4). *: A significant difference of $P<0.01$ compared to the mismatch ribozyme is observed.

Figure 7A:
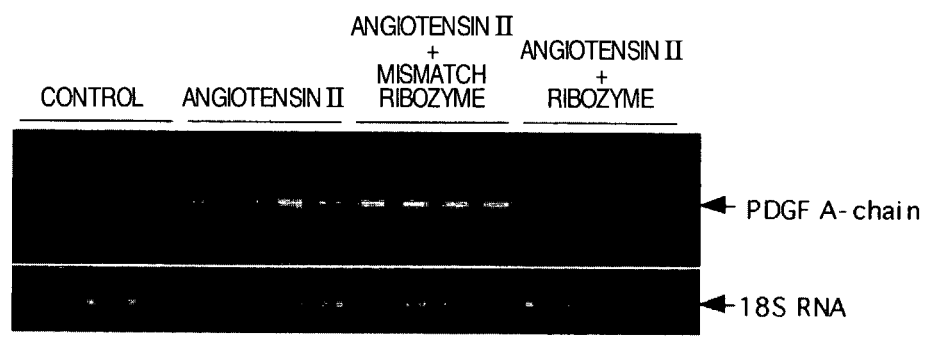
Figure 7B:
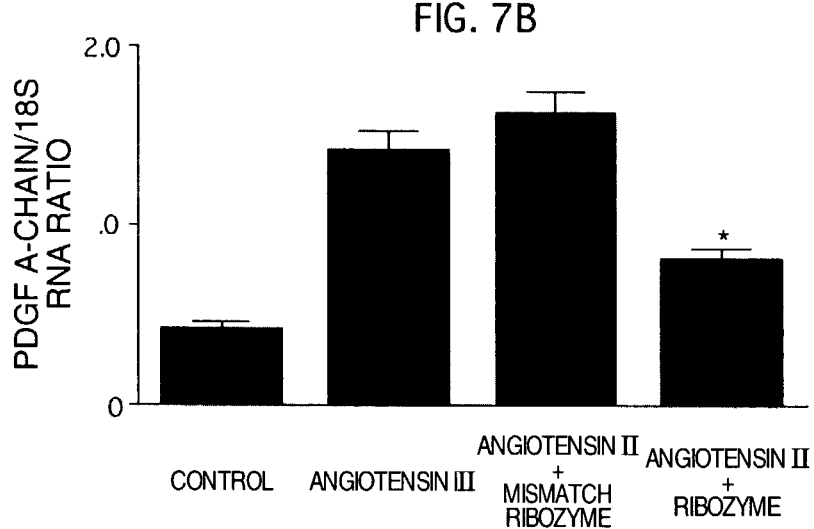

FIGS. 7A and 7B show the effect of a hammerhead ribozyme to human PDGF A-chain mRNA on angiotensin II-stimulated expression of PDGF A-chain mRNA in human VSMC. FIG. 7A shows the result of an experiment in which the VSMC at the stationary phase was incubated together with angiotensin II and 1.0 μM ribozyme or mismatch ribozyme with Lipofectin for 20 hours. The amounts of PDGF A-chain mRNA and 18S rRNA were measured by reverse transcription-polymeruse chain reaction (RT-PCR) analysis. FIG. 7B shows the result of an experiment in which the ratio of PDGF A-chain mRNA to 18S rRNA was evaluated by densitometric analysis. Data are expressed in mean ±SEM (n=4). *: A significant difference of $P<0.01$ compared to the mismatch ribozyme is observed.

Figure 8A:
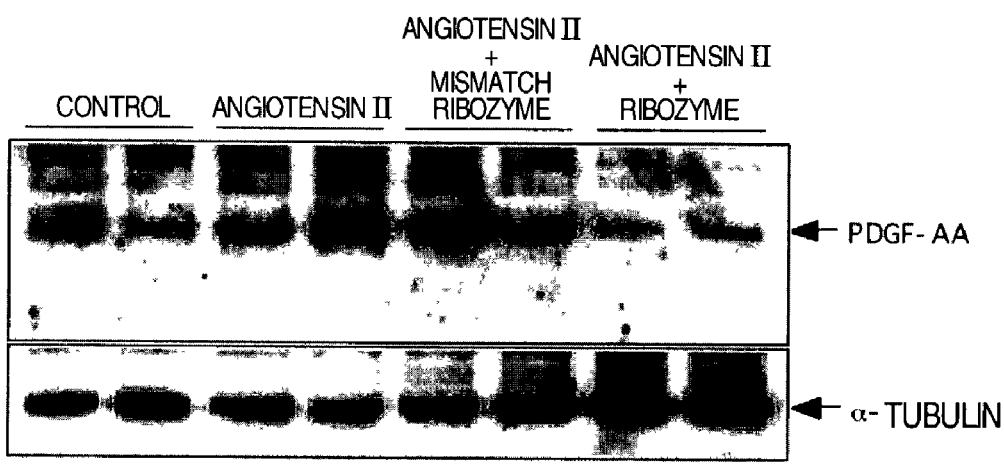
Figure 8B:
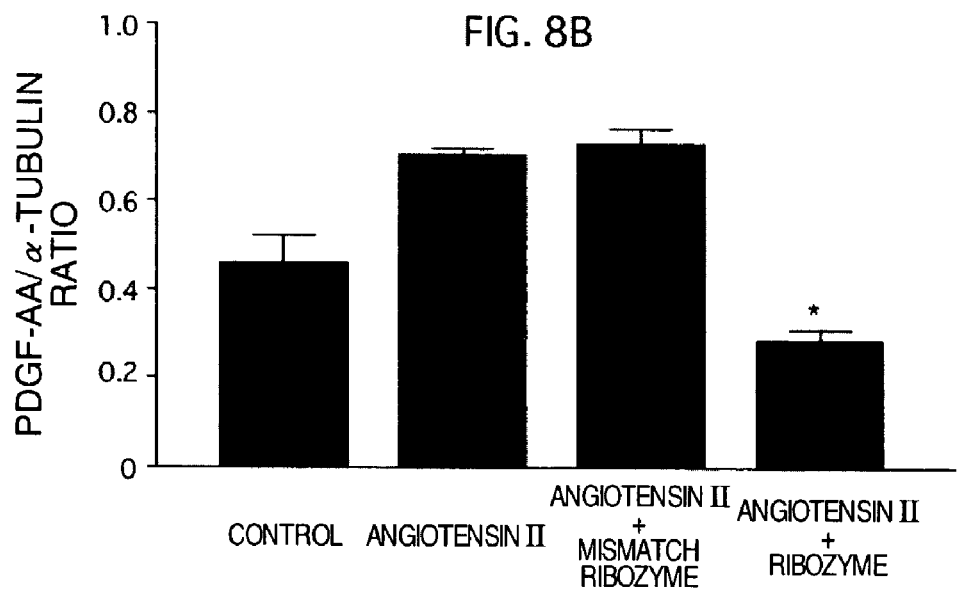

FIGS. 8A and 8B show the effect of a hammerhead ribozyme to human PDGF A-chain mRNA on expression of PDGF-AA protein in human VSMC. The VSMC at the stationary phase was incubated together with angiotensin II and 1.0 μM ribozyme or mismatch ribozyme with Lipofectin for 20 hours. The amounts of PDGF-AA protein and α-tubulin protein were measured by Western blot analysis. FIG. 8B shows the result of an experiment in which the ratio of PDGF-A chain mRNA to α-tubulin mRNA was evaluated by densitometric analysis. Data are expressed in mean ±SEM (n=4). *: A significant difference of $P<0.01$ compared to the mismatch ribozyme is observed.

Figure 9A:
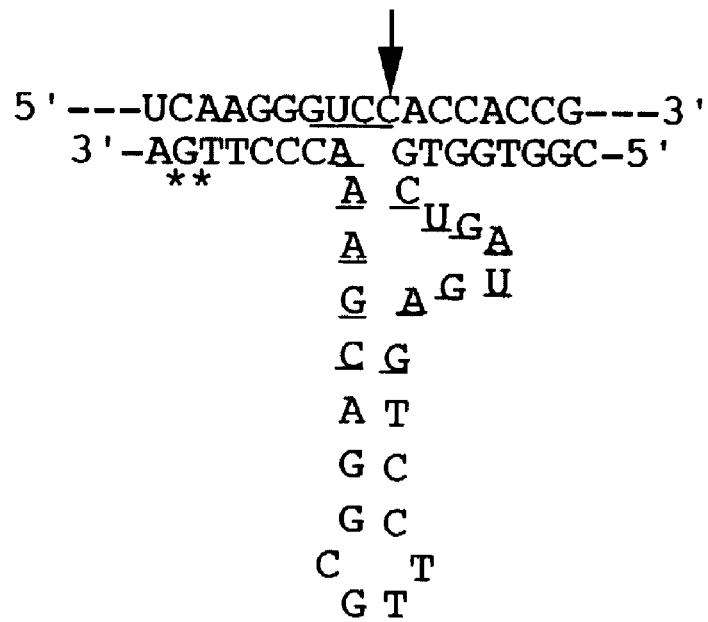
Figure 9B:
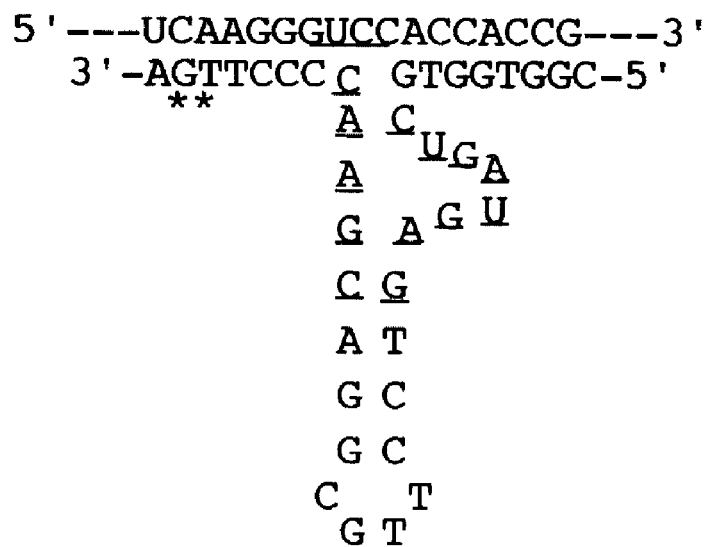

FIG. 9A (Top Sequence =SEQ ID NO: 11 (bases 17–33); Bottom Sequence =SEQ ID NO:9) and FIG. 9B (Top Sequence =SEQ ID NO: 11 (bases 17–33); Bottom Sequence =SEQ ID NO: 10) show the basic structure of the hammerhead ribozyme (FIG. 9A) and the mismatch ribozyme (FIG. 9B) designed in Example 2. The upper column shows part of the target rat PDGF A-chain mRNA in which cleavage takes place immediately after the GUC sequence at bases 919–921 of rat PDGF A-chain mRNA (arrow). The lower column is the ribozyme in which the underlined bases are the RNA structure and the rest is DNA structure as a DNA-RNA chimeric structure. * mark means that the structure between two bases at the 3'-end is modified to the phosphorothioate in order to render it resistant to nuclease.

BEST MODE FOR CARRYING OUT THE INVENTION

The exaggerated growth of cardiovascular organs observed in patients with essential hypertension and SHR can cause serious complications such as apoplexy, ischemic heart diseases, and nephrosclerosis. These complications are basically associated with the exaggerated growth of VSMC, and are the targets of the treatment for hypertension.

In order to evaluate the involvement of the PDGF A-chain in the exaggerated growth of cardiovascular organs in hypertension, we have shown that an antisense ODN complementary to PDGF A-chain mRNA suppresses the exaggerated growth of cardiovascular organs in SHR in vitro and in vivo, which suggested the involvement of the PDGF A-chain in the exaggerated growth of cardiovascular organs in hypertension. We have also shown that the DNA-RNA chimeric ribozyme designed to target rat PDGF A-chain mRNA can cleave the PDGF A-chain mRNA of cultured VSMC in a base sequence-specific manner, which results in reduced expression of PDGF-AA protein in VSMC and suppresses the exaggerated growth of SHR-derived VSMC.

There is no effective pharmacotherapy at present for the restenosis of coronary arteries due to neointimal formation after PTCA, posing a serious problem in the field of cardiovascular diseases. It is known that PDGF A-chain is involved in the restenosis of coronary arteries by the migration and proliferation of VSMC into the intimal membrane side (Scott N A, Cipolla G D, Ross C E, Dunn B, Martin F H, Simonet L, Wilcox J N. (1996) 93:2178). In the present study, we have designed and synthesized a 38-base hammerhead ribozyme in order to cleave human PDGF A-chain mRNA after the GUC sequence, more specifically at nucleotide 591. In the presence of $MgCl_2$, the synthetic ribozyme to human PDGF A-chain mRNA cleaved the synthetic target RNA into two RNA fragments with a predicted size in a dose-dependent manner. When 0.01–1.0 μM of ribozyme was administered to human PDGF A-chain mRNA, angiotensin II— or TGF-β-stimulated DNA synthesis by Human VSMC was significantly inhibited in a dose-dependent manner.

The administration of 1.0 μM of ribozyme to human PDGF A-chain mRNA significantly inhibited both of angiotensin II-stimulated PDGF A-chain mRNA expression and PDGF-AA protein expression. These results indicated that ribozyme designed to target human PDGF A-chain mRNA inhibits effectively and specifically the growth of human VSMC stimulated by angiotensin II or TGF-β by cleaving PDGF A-chain mRNA, leading to the suppression of PDGF-AA protein expression in human VSMC. This shows that this ribozyme can be used as a gene-therapy for the vascular proliferative diseases.

There are two different methods of ribozyme derivery in a living body: one is a method in which a synthetic ribozyme encapsulated in a cationic lipid membrane is extraneously introduced (Malone, R W., Felgner, P L., Vermn, I M (1989) Proc. Natl. Acad. Sci., USA 86, 6077), and the other is a method in which a vector DNA comprising DNA encoding ribozyme is introduced into the cell using a virus vector etc., and then the ribozyme is expressed in the cell (Friedmann,. T and Roblin. R. (1972) Science 175, 949). As the representative methods, the following can be mentioned:

(1) Lipofection Method

The surface of the cell is negatively charged. Thus, the ribozyme of interest or a vector (double stranded circular DNA plasmid) containing DNA encoding the ribozyme is combined with a cationic lipid (lipofection reagent (Lipofectin, etc.)) to form a complex, which is introduced into the cell.

(2) Virus Vector Method

Among the genetic information of the virus, those required for gene expression is only left, into which a sequence encoding a ribozyme having a therapeutic effect is integrated. This vector is integrated into the DNA of interest by means of viral power.

Using the ribozyme of the present invention, target RNA, specifically human PDGF A-chain mRNA, can be specifically cleaved.

The ribozyme of the present invention can be used as a pharmaceutical agent, specifically a gene therapeutic agent, for preventing and/or treating vascular proliferative diseases. For example, by encapsulating the ribozyme of the present invention into the Lipofection reagent and administering this into the living body to allow it to be incorporated into the cells in the affected area, the translation of PDGF-A chain mRNA can be inhibited. Alternatively, by integrating DNA encoding the ribozyme of the present invention into a vector such as virus, and introducing it into the cell in the affected area, the translation of PDGF A-chain mRNA can be inhibited. The administration of the ribozyme of the present invention may be performed at appropriate doses, regimens, and frequencies over the period until the effectiveness of the prevention and/or treatment can be observed or the disease states can be alleviated, though it depends on the severity of the disease and the responsiveness of the living body.

The present invention will now be explained more specifically with regard to the following Examples. It is to be noted that the scope of the present invention is not limited by these examples in any way.

EXAMPLE 1

Reference: Antisense Method

We have investigated the in vitro and in vivo effect of suppressing vascular proliferation in SHR by antisense ODN to PDGF A-chain mRNA and the mechanisms.

Method

A phosphorothioate type antisense ODN complementary to 15 base sites at the start codon region of PDGF A-chain mRNA and, as control, a nonsense ODN having the same base composition but in a different order were used.

Antisense ODN: 5'-AGGTCCTCATCGCGT-3'(SEQ ID NO: 7)

Nonsense ODN: 5'-TGCCGTCAGCTGCTA-31 (SEQ ID NO: 8)

Experiment I: The cell cycles of SHR-derived and Wistar-Kyoto rats (WKY)-derived VSMC were synchronized with 0.2% calf serum, and DNA synthesis was measured by $^3$H-thymidine incorporation, PDGF-A protein was measured by the Western blot analysis, and PDGF A-chain mRNA was measured by RT-PCR analysis to investigate the effect of 0.01–1.0 μM of antisense ODN. Furthermore, the effect of antisense ODN containing one or three mutated base(s) was also investigated.

Experiment II: One hundred ng of antisense ODN was labelled with $^{32}$P using polynucleotide kinase, and then was intraperitoneally given to rats. At 1, 4, and 16 hours later, the incorporation into the cardiovascular organs and the nuclei were evaluated. Experiment III: 15-week old SHR and WKY were divided into the sham group (physiological saline was subcutaneously given using an ALZET pump for 28 days), the nonsense group (nonsense ODN 80 ng/g body weight was subcutaneously given for 28 days), and the antisense group (the same amount of antisense ODN was subcutaneously given for 28 days). Blood pressure was determined every 7 days. On day 28, $^3$H-thymidine was intraperitoneally given. The aorta, the heart, and the kidney were extracted, and the radioactivity of $^3$H ($^3$H-total), DNA content, $^3$H-DNA, and PDGF-AA protein were measured.

Result

Experiment I: The antisense ODN significantly suppressed excessive DNA synthesis in SHR-derived VSMC compared to the nonsense ODN, but did not suppress in WKY-derived VSMC. In the antisense ODN containing mutated bases, the effect of suppressing the growth of SHR-derived VSMC weakened in proportion to the number of mutated bases. In the Western blot analysis expression of PDGF-AA protein was only observed in SHR-derived VSMC, which was suppressed by antisense ODN in a concentration dependent manner, but was not suppressed by the nonsense ODN. The antisense ODN did not affect the expression of PDGF A-chain mRNA.

Experiment II: $^{32}$P-antisense ODN was incorporated into the organs within one hour, and the efficiency of incorporation peaked at 4 hours, and it was twice in the aorta compared to other organs, and lasted up to 16 hours.

Experiment III: The antisense ODN did not change blood pressure in SHR and WKY. DNA content and DNA synthesis was higher in the aorta of SHR compared to WKY, which was remarkably suppressed by the antisense ODN, but was not in WKY. The nonsense ODN did not suppress them. In the Western blot analysis, PDGF-AA protein expression in the aorta was only detected in SHR, and the antisense ODN remarkably suppressed it. The antisense ODN did not affect them in the heart, the kidney and the liver. It can be concluded from these findings that the antisense ODN to PDGF A-chain mRNA markedly suppresses the exaggerated vascular proliferation in SHR without any changes in blood pressure, suggesting the possibility of gene therapy for arterial proliferation diseases including hypertensive vascular diseases.

EXAMPLE 2

Reference: Effect of Chimeric Ribozyme on Rat PDGF A-chain mRNA)

We have investigated the effect of DNA-RNA chimeric ribozyme to rat PDGF A-chain mRNA on the exaggerated growth of SHR-derived VSMC.

Method

A hammerhead ribozyme (FIG. 9A, lower sequence) and a mismatch ribozyme (FIG. 9B, lower sequence) complementary to the loop structure containing the GUC sequence in rat PDGF A-chain mRNA were designed. The underline indicates an RNA structure, and the rest indicates a DNA structure. * means phosphorothioate chemical modification.

Hammerhead-type ribozyme: 5'-CGGTGGTGCUGAU GAGTCCTTGCGGACAAACCCTT*G*A-3' (SEQ ID NO: 9)

Mismatch ribozyme: 5'-CGGTGGTGCUGAUGAGTCC TTGCGGACAACCCCTT*G*A-3' (SEQ ID NO: 10)

From a template DNA ligated to T7 promoter, the following target RNA was synthesized using T7 RNA polymerase, and the ribozyme and the target RNA were incubated in the absence or the presence of MgCl$_2$. The target RNA is the following base sequence generated using as a template positions 897–981 of rat PDGF A-chain cDNA and can be cleaved immediately after the underlined GUC sequence.

Target RNA: 5'-CGUCAAGUGCCAGCCCUCAAGGGUC CACCACCGCAGUGUCAAGGUGGCCAAAGUGGAG UAUGUCAGGAAGAAGCCAAAAUUGAAA-3' (SEQ ID NO: 11)

In the cell experiment, a chimeric ribozyme in which only the active site is RNA structure and the rest is a DNA structure was synthesized and used. In the ribozyme incorporation experiment, a chimeric ribozyme was labelled with FITC and then was treated with VSMC by Lipofectin to investigate the incorporation into the cell.

Effect of ribozyme on VSMC growth: The chimeric ribozyme was treated with WKY- and SHR-derived VSMC, and the effect of ribozyme on 1) the incorporation of $^3$H-thymidine into DNA by DNA synthesis, 2) increase in the number of cells with serum stimulation, 3) the expression of PDGF A-chain mRNA by the RT-PCR analysis, 4) the expression of PDGF-AA protein by the Western blot analysis were investigated.

Result

1) In the presence of Mg$^{2+}$, the unmodified ribozyme (this was not made into a DNA-RNA chimera, not chemically modified to phosphorothioate, and has the following base sequence: 5'-CGGUGGUGCUGAUGAGUCCUUGCGGA CGAAACCCUUGA-3' (SEQ ID NO: 12)) and the chimeric ribozyme cleaved the target RNA, but did not cleave in the absence of Mg$^{2+}$.

2) The FITC-ribozyme was incorporated into the cytoplasm, and migration in the nucleus was little.

3) 0.1 and 1 µM chimeric ribozyme inhibited the basic DNA synthesis in serum-free SHR-derived VSMC in a concentration-dependent manner, while in the WKY-derived VSMC suppression was moderate, and the mismatch ribozyme did not affect it.

4) 1 µM chimeric ribozyme inhibited the expression of PDGF A-chain mRNA in the SHR-derived VSMC, but the mismatch ribozyme did not suppress it.

5) 1 µM chimeric ribozyme inhibited the expression of PDGF-AA protein in the SHR-derived VSMC, but the mismatch ribozyme did not affect it.

From these findings, it was concluded that the ribozyme to PDGF A-chain mRNA specifically suppresses the exaggerated growth of SHR-derived VSMC at low concentration, suggesting that the ribozyme may be useful for gene therapy of vascular proliferative diseases including hypertension in the future. Example 3 (the ribozyme of the present invention to human PDGF A-chain mRNA)

Method

Designing a Hammerhead-type Ribozyme to Human PDGF-A Chain mRNA

Figure 1:
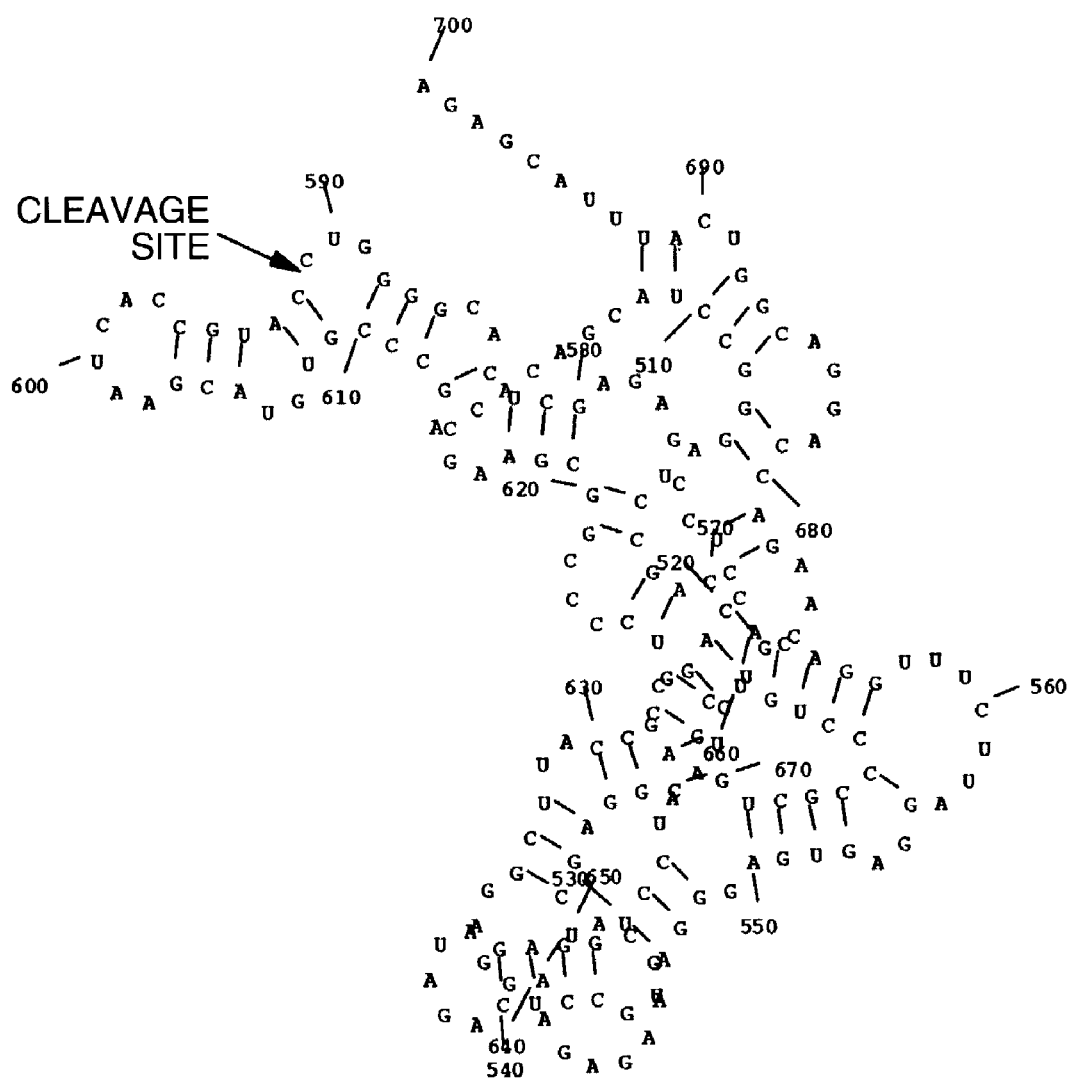
FIG. 1 is a photograph showing the secondary structure of human PDGF A-chain mRNA (nucleotide 501–700, SEQ ID NO:15) by GENETYX-MAC and the cleavage-site GUC sequence of nucleotide 591, represented by an arrow.

In order to avoid a double-stranded structure at the cleavage site, the GUC sequence (see FIG. 1) in the loop structure located at nucleotide 591 of the human PDGF A-chain mRNA (the lower sequence at each of FIGS. 2A and B) (Betzholtz C., Johnson A., Heldin C—H, Westermark B., Lind P., Urdea M S, Eddy R., Shows T B, Philpott K., Mellor A L, Knott T J, and Scott J. "cDNA Sequence and Chromosomal Localization of Human Platelet-Derived Growth Factor A-Chain and Its Expression in Tumor Cell Lines." Nature 320:695–699, 1986) was chosen as a cleavage site according to "GENETYX-MAC; Second Structure and Minimum Free Energy", and in order to cleave this, a 38-base hammerhead-type ribozyme (5'-GUGGCAUGCU GAUGAGUCCUUGCGGACGAAACCCCGUG-3') (SEQ ID NO: 1) (see FIG. 2A, the upper sequence) was designed and as control a mismatch ribozyme were designed (SEQ ID NO: 13) (FIG. 2B, the lower sequence). This has a one base substitution from A to C at position 31 from the 5'-end in the above ribozyme sequences.

Synthesis of a Hammerhead Ribozyme and a Target RNA using T7 RNA Polymerase

Using T7 RNA polymerase and a synthetic DNA template, a hammerhead ribozyme and a target RNA were synthesized as described (Uhlenbeck O C (1987) Nature 328:596). As a sufficiently active template DNA chain, a fragment containing the region from −17 to −1 of class III T7 RNA polymerase promoter followed by the complement of the desired RNA sequence was constructed. The full-length of the target DNA template contains a complement comprising a 17-base promoter region and the succeeding 85-base human PDGF A-chain mRNA (from nucleotide 567 to 651). The full-length of the ribozyme template DNA contains a complement comprising a 17-base promoter region and the succeeding 38-bases of the ribozyme sequence.

In order to construct a transcription template, a complementary chain comprising 17-nucleotide fragments corresponding to −17 to −1 of the promoter was annealed to the promoter region of the template DNA chain. In order to prepare an annealed template, these two chains were mixed in an equimolar concentration, heated at 90° C. for 2 minutes, annealed at 60° C. for 3 minutes, and then immediately cooled on ice.

For the synthesis of RNA, 3 μg of the annealed template was mixed with 6 μl of T7 RNA polymerase (50 U/μl, Takara Biochemical, Osaka), 5 μl of α-$^{32}$P-CTP (specific activity: 3000 Ci/mmol, New England Nuclear, Del.), 50 U of RNase inhibitor (Takara Biochemical, Osaka), and 50 μl of the transcription reaction buffer (40 mM Tris-HCl, pH 8.0, 0.5 mM rNTP, 8 mM $MgCl_2$, 5 mM dithiothreitol, 2 mM spermidine), incubated at 37° C. for 4 hours. Then, this was mixed with 100 μl of phenol and chloroform (1:1), and centrifuged at 16000 rpm for 30 minutes. The supernatant was transferred to a new test tube and mixed with an equal amount of chloroform/isoamyl alcohol (25:1). After centrifugation at 16000 rpm for 30 seconds, the supernatant was mixed with 200 μl of 100% ethanol, which was centrifuged at 16000 rpm for 15 minutes to prepare RNA pellets. This RNA was washed twice in 75% ethanol, ethanol was evaporated, and RNA was dissolved in 5 μl of $H_2O$ treated with diethylpyrocarbonate (DEPC).

Figure 3:
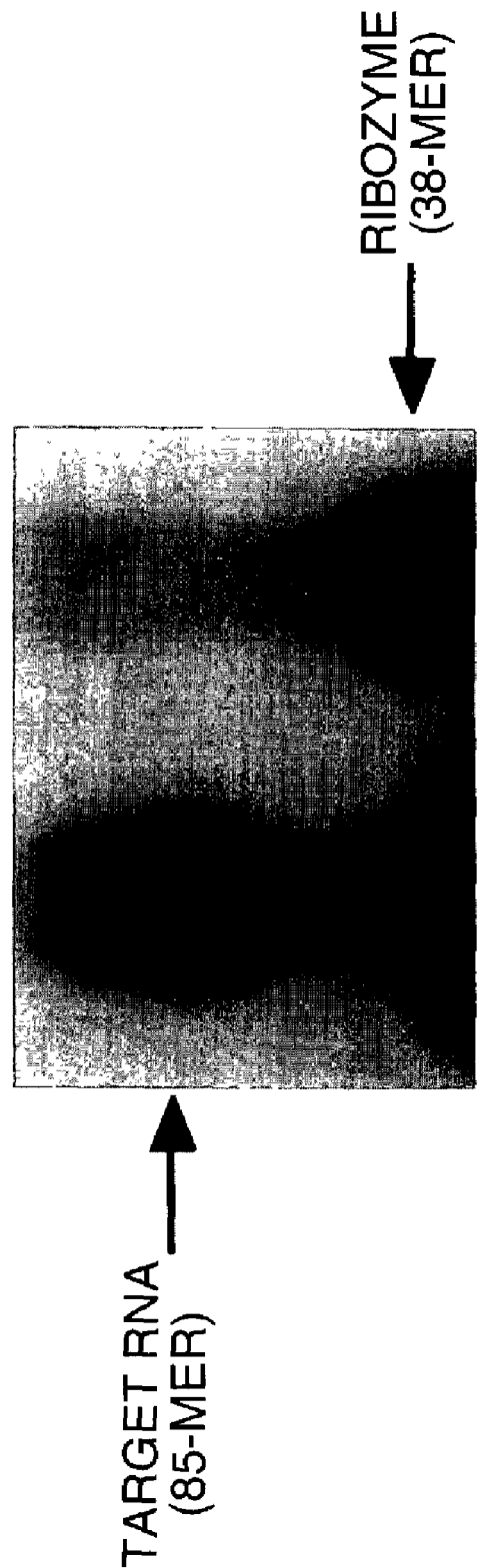
FIG. 3 shows synthetic ribozyme to human PDGF A-chain mRNA, and target RNA, which were produced using T7 RNA polymerase.

Prior to electrophoresis, 5 μl of RNA was heated to 90° C. for 2 minutes, and then placed on a 6% polyacrylamide sequencing gel. After electrophoresis at 300 V for 1 hour, the gel was exposed to a film for 10 minutes (FIG. 3), and for recycling of RNA, the gel was excised at the position of the band of the radioactivity-exposed film. The RNA-containing gel was destroyed in 400 μl of the DEPC-treated water, and shaken at 50° C. for 2 hours to extract RNA. After centrifugation at 14000 rpm at 4° C. for 15 minutes, the supernatant was transferred to a new test tube, and mixed with 40 μl of 3 M sodium acetate and 1000 μl of 99% ethanol, and kept at 20° C. for 1 hour. After centrifugation at 14000 rpm at 4° C. for 15 minutes, RNA pellets were washed twice in 75% ethanol, ethanol was evaporated, RNA was dissolved in 50 μl of DEPC-treated water, and stored at −80° C. The RNA concentration was measured by UV spectroscopy using the UV-1200 spectrophotometer (Shimadzu Seisakusho, Tokyo).

In Vitro Cleavage Reaction

An in vitro cleavage reaction was carried out as described (Saxena S K, Ackerman E J. (1990) J Biol Chem. 265: 17106). The annealing of the hammerhead ribozyme to the target RNA was carried out by adding 1 μl of 2.4 μM ribozyme and 1 μl of 240 nM target RNA to 20 μl of 50 mM Tris-HCl, pH 8.0, followed by heating at 90° C. for 1 minute. Then, the reaction mixture was slowly (over 30 minutes) cooled to 37° C. The cleavage reaction was initiated by addition of 2 μl of 250 mM $MgCl_2$ to the annealed ribozyme and the target RNA in the cleavage reaction buffer, which was then incubated at 37° C. for 1, 5, and 15 hours. Each sample was heated at 90° C. for 2 minutes, and then was immediately cooled on ice. Then, 5 μl of each sample was placed on the sequencing gel and was electrophoresed. The gel was dried, and was exposed to a film for autoradiography.

Establishment of Cell Culture and Quiescent

Human VSMC (BioWhittaker, Inc., MD, USA) isolated from a human aorta and subcultured was maintained in a smooth muscle basal medium (SmBM, BioWhittaker, Inc., MD, USA) containing 10% bovine fetal serum (Gibco, Life Technologies, Inc., Gaithersburg, Md., USA) and 50 μg/ml streptomycin (Gibco). When the cells reached confluence in 7–10 days, the cells exhibited a typical hill-and-valley pattern in culture. These cells were subcultured by trypsinization using 0.05% trypsin (Gibco) dissolved in Dulbecco's phosphate buffered saline (PBS) containing no $Ca^{2+}$ or $Mg^{2+}$, placed in a 75 $cm^2$ tissue culture flask, and then incubated at a density of $10^5$ cells/ml. The trypsinized cells were plated on a 24-well tissue culture plate at a density of $10^5$ cells/well. The cells were grown in SmBM containing 10% bovine fetal serum in a $CO_2$ incubator at 37° C. until they reach 40–60% confluence, and after replacing the culture medium was with a serum-free SmBM medium, it was incubated for 48 hours and the quiescent was established.

Delivery of Ribozyme into VSMC

For transfection into VSMC, all hammerhead ribozymes were synthesized using an RNA synthesizer and purified by high performance liquid chromatography. For each transfection, ribozyme was diluted to 0.01–1.0 μM with 100 μl of serum-free DMEM, and 5 μl of Lipofectin (Gibco) was diluted with 100 μl of serum-free DMEM, and then were allowed to stand at room temperature for 45 minutes. Both dilutions were mixed and then incubated at room temperature for 15 minutes. The quiescent VSMC was washed twice in a serum-free Dulbecco's modified Eagle medium (DMEM). Then the Lipofectin-ribozyme complex (200 μl) was added to the cells, and incubated at 37° C. in a $CO_2$ incubator.

Measurement of DNA Synthesis

The incorporation of $^3$H-thymidine into newly synthesized DNA was measured as previously described (Ross R. (1971) J Cell Biol. 50:172). VSMC treated with or without ribozyme in a 24-well plate were incubated together with DMEM containing $^3$H-thymidine (0.5 μCi/ml) (New England Nuclear, Foster, Calif., USA) for 2 hours. After removing excessive $^3$H-thymidine by washing each well using 1 ml of 150 mM NaCl, the cells were fixed in 1 ml of ethanol:acetic acid (3:1) solution for 10 minutes. After washing with 1 ml of $H_2O$, acid-insoluble material was precipitated using 1 ml of cold perchloric acid, and heated at 90° C. for 20 minutes to extract DNA into 1.5 ml of perchloric acid. The perchloric acid containing the solubilized DNA was transferred to a scintillation vial and mixed with 10 ml of scintillation cocktail, and radioactivity was measured using a liquid scintillation counter.

RT-PCR Analysis of PDGF A-chain mRNA Expression

VSMC treated with or without ribozyme in a 24-well plate were washed once in PBS, and VSMC in each well were dissolved in 800 µl of RNAzolB (Biotecx Laboratories Inc., Houston, Tex., USA). Each sample was mixed with 80 µl of 100% chloroform by vortex mixing for 15 seconds, allowed to stand on ice for 15 minutes, and then was subjected to centrifugation at 12,000 g for 15 minutes to extract total RNA. The upper colorless aqueous phase was mixed with an equal amount of 100% isopropanol, maintained at −20° C. for 45 minutes, and was centrifuged at 12,000 g at 4° C. for 15 minutes to precipitate RNA. The RNA pellets were washed twice in 500 µl of 75% ethanol, centrifuged at 12,000 g at 4° C. for 8 minutes, dried, and dissolved in 10 µl of TE buffer (10 mM Tris-HCl, pH 8.0, 1 mM EDTA). After denaturation at 65° C. for 15 minutes, the RNA sample was treated with 0.5 U DNase (Gibco) dissolved in 0.5 µl of DNase buffer (20 mM Tris-HCl, pH 8.3, 50 mM KCl and 2.5 mM $MgCl_2$) at room temperature for 45 minutes. Then, 0.5 µl of 20 mM EDTA was added, and heated at 98° C. for 10 minutes to inactivate DNase.

RT-PCR analysis was performed as previously described (Mocharla H, Mocharla R, Hocks M E. (1990) Gene 93:271). RNA (1 g/20 µl) was reverse transcribed into a single stranded cDNA with 0.25 U/µl of avian myeloblastoma virus reverse transcriptase (Life Sciences Inc., St. Petersburg, Fla., USA), 5 mM $MgCl_2$, 50 mM KCl, 1 mM deoxy NTPs, and 2.5 µM random hexamer dissolved in 10 mM Tris-HCl, pH 8.3. Five microliters of the diluted cDNA product was mixed with 10 mM Tris-HCl, pH 8.3, 50 mM KCl, 4 mM $MgCl_2$, and 0.025 U/µl Taq DNA polymerase (Takara Biochemical, Osaka), and 0.2 M upstream sense primer and downstream antisense primer to make a total volume of 25 µl. Human PDGF A-chain mRNA was amplified by PCR to obtain a 415-bp product with a sense primer (5'-GCAGTCAGATCCACAGCATC-3') (SEQ ID NO: 3) and an antisense primer (5'-TCCTCTAACCTCACCTG-GAC-3') (SEQ ID NO: 4) containing the GUC cleavage site. A sense primer (5'-TCAAGAACGAAAGTCGGAGG-3') (SEQ ID NO: 5) and an antisense primer (5'-GGA-CATCTAAGGGCATCACA-3') (SEQ ID NO: 6) to human 18S ribosome RNA were used as the internal controls. PCR was performed using an automated thermal cycler (Perkin Elmer). PCR amplification was performed by the first denaturation at 96° C. for 5 minutes, then 30 cycles of denaturation at 94° C. for 60 seconds, annealing at 58° C. for 2 minutes, and primer elongation at 72° C. for 1 minute, and then the last primer elongation was performed at 72° C. for 10 minutes. The PCR product obtained was electrophoresed on a 1.5% agarose gel.

Western Blot Analysis of PDGF-AA Protein in VSMC

After treatment of human VSMC at a cell density of $10^5$ cells/$cm^2$ in a 6-well plate with ribozyme, VSMC were washed in PBS, and dissolved in 1 ml of dissolution buffer (50 mM Tris-HCl, pH 8.0, 150 mM NaCl, 0.02% sodium azide, 100 µg/ml phenyl methyl sulphonyl fluoride, 1 µg/ml aprotinin, 1% Triton X-100) per well. Total protein was extracted and purified with 100 µl of chloroform and 400 µl of methanol. Then protein concentration was determined by the method reported by Lowry et al. (Lowry O H, Rosenbrough N H, Farr A L, Randall J. (1951) J. Biol. Chem. 193:265). For Western blot analysis, 5 µg of protein was used together with 20 µl of the sample buffer. The sample was boiled, and subjected to a 6% polyacrylamide gel electrophoresis. Then protein was transferred to a nitrocellulose membrane. After incubating at 4° C. overnight with 100% Block Ace TM (Dainippon Insatsu K.K., Osaka), the membrane was incubated with a rabbit polyclonal antibody (Austral Biologicals, San Ramon, Calif., USA) or mouse anti-a tubulin monoclonal antibody (Sigma Biosciences, Louis, Mich., USA) specific to PDGF-AA diluted 200-fold in a TBST solution (10 mM Tris-HCl, pH 8.0, 150 mM NaCl, and 0.05% Tween 20) containing 15% Block Ace at room temperature for 3 hours. After washing in the TBST solution for 10 minutes twice, the membrane was incubated at room temperature for 1 hour with goat anti-rabbit IgG or goat anti-mouse IgG (Bio-Rad Laboratories) diluted 3000-fold in the TBST solution containing 15% Block Ace, and washed for 10 minutes three times in the TBST solution. Immune complexes on the membrane were detected as previously described with protein A-gold (Bio-Rad Laboratories) (Danscher G, Ngaard JUR. (1983) J Histochem Cytochem 31:1394). The membrane was incubated with protein A-gold dissolved in 4 volumes of the protein gold buffer (20 mM Tris-HCl, pH 8.1, 150 mM NaCl, 0.1% BSA, 0.1% Tween 20, and 0.02% sodium azide) at 20° C. for 1 hour. Then the membrane was washed for 10 minutes in the protein gold buffer containing 1% Triton X-100, twice for 5 minutes in the protein gold buffer alone, and twice for 1 minute in deionized distilled water to remove chlorine ions, and then for 5 minutes in a citrate buffer (0.2 M citric acid and 0.2 M sodium citrate, pH 3.7). Then the membrane was stained with 40 mg of silver lactate dissolved in 30 ml of a hydroquinone solution (300 mg of hydroquinone dissolved in 300 ml of the citrate buffer).

Statistical Analysis

The results are expressed in mean ±SEM. Statistical significance between means was evaluated by Student's t test on unpaired data and a two-way analysis of variance (ANOVA), and then by Duncan's multiple range test.

Result

In Vitro Cleavage Reaction

Figure 4:
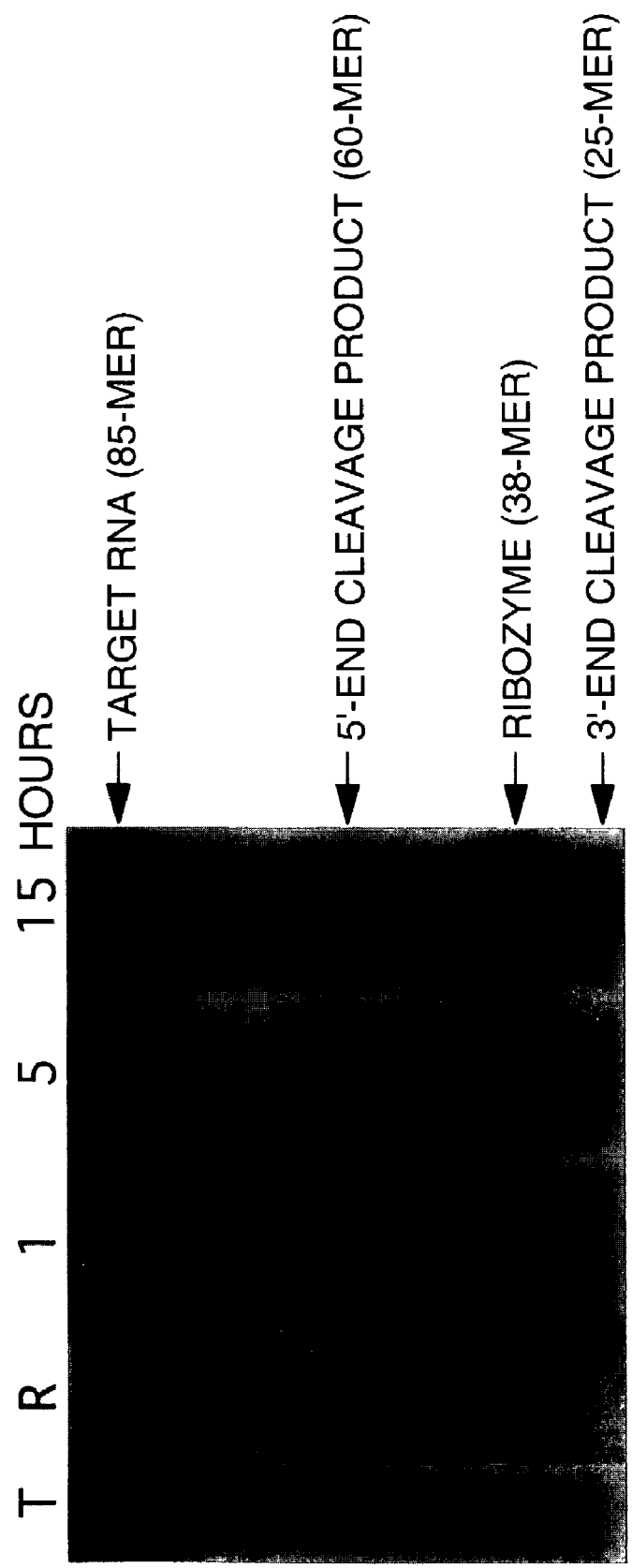
FIG. 4 shows the result of an experiment in which an in vitro cleavage reaction was analyzed by electrophoresis using a sequence gel, and then the dry gel was placed in close contact with a film for autoradiography. For the cleavage reaction, a synthesized 85-base target RNA (T) and a synthesized 38-base total RNA ribozyme (R) to human PDGF A-chain mRNA were used. The annealed target RNA (10 nM) and total RNA ribozyme (100 nM) were incubated in the presence of 25 mM $MgCl_2$ at 37° C. for 1, 5 and 15 hours. In the presence of $MgCl_2$, the synthetic ribozyme cleaved the target RNA into two fragments that correspond to the predicted size (60 and 25 bases) in a time-dependent manner.

An in vitro cleavage reaction with a synthetic hammerhead ribozyme to human PDGF A-chain mRNA and standard RNA is shown in FIG. 4. In the presence of $MgCl_2$, the synthetic ribozyme cleaved the target RNA into two RNA fragments corresponding to the predicted size (60 and 25 bases) in a time-dependent manner.

Figure 5:
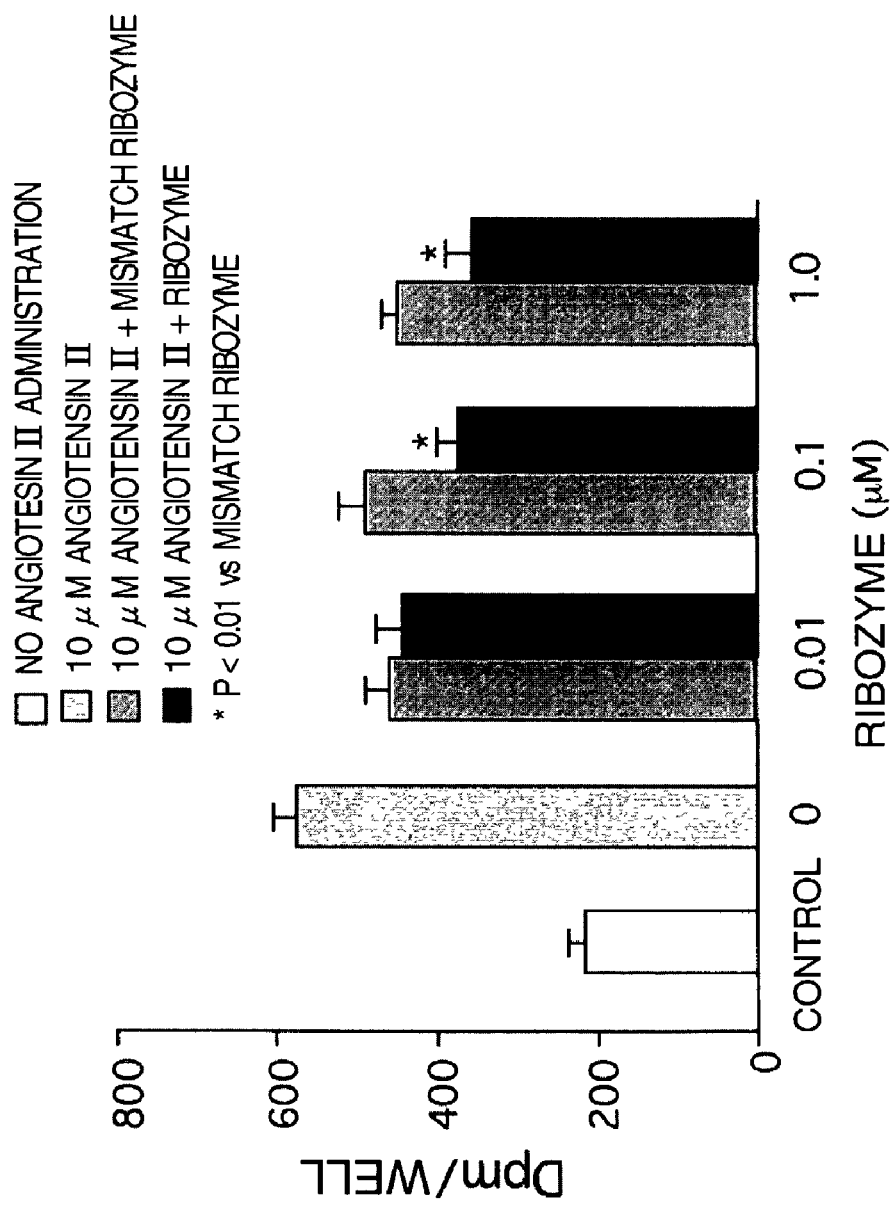
FIG. 5 shows the effect of a hammerhead ribozyme to human PDGF A-chain mRNA on angiotensin II-stimulated DNA synthesis in human VSMC. The VSMC at the stationary phase was incubated together with angiotensin II and 0.01–1.0 μM ribozyme or mismatch ribozyme with Lipofectin for 20 hours. Data are expressed in mean ±SEM (n=4).

Effect of the Hammerhead Ribozyme to Human PDGF A-chain on DNA Synthesis by VSMC The effect of the hammerhead ribozyme (0.01–1.0 µM) to human PDGF A-chain with Lipofectin on angiotensin II-stimulated DNA synthesis in human VSMC is shown in FIG. 5. Addition of 10 µM of angiotensin II significantly (P<0.01) increased DNA synthesis in human VSMC, and 0.1 and 1.0 µM hammerhead ribozyme significantly (P<0.01) inhibited the angiotensin II-stimulated DNA synthesis in human VSMC compared to the mismatch ribozyme.

Effect of hammerhead ribozyme (0.01–1.0 µM) to human PDGF A-chain with Lipofectin on TGF-β-stimulated DNA synthesis in human VSMC is shown in FIG. 6. Addition of 10 µM TGF-β significantly (P<0.05) increased DNA synthesis in human VSMC, and 0.01 and 1.0 µM hammerhead ribozyme significantly (P<0.01) inhibited TGF-β-stimulated DNA synthesis in human VSMC compared to mismatch ribozyme.

Effect of the Hammerhead Ribozyme on the Expression of PDGF A-chain mRNA in Human VSMC FIGS. 7A and 7B show the effect of the hammerhead ribozyme to PDGF A-chain on angiotensin II-stimulated PDGF A-chain mRNA expression in human VSMC. Addition of 10 µM angiotensin II significantly (P<0.01) increased PDGF A-chain mRNA expression in human VSMC. The mismatch ribozyme did not affect the expression of angiotensin II-stimulated PDGF-AA protein. Addition of 1.0 μM hammerhead ribozyme to PDGF A-chain significantly (P<0.01) suppressed angiotensin II-stimulated PDGF A-chain mRNA in human VSMC compared to the mismatch ribozyme.

Effect of the Hammerhead-type Ribozyme to Human PDGF-A Chain on PDGF-A Protein Expression in Human VSMC FIG. 8A shows effect of the hammerhead-type ribozyme on angiotensin II-stimulated PDGF-AA protein expression in human VSMC. Addition of 10 μM of angiotensin II enhanced the expression of PDGF-AA protein in human VSMC. The mismatch ribozyme did not affect the expression of angiotensin II-stimulated PDGF-AA protein. Addition of 1.0 μM hammerhead-type ribozyme to PDGF-A chain remarkably inhibited the expression of angiotensin II-stimulated PDGF-AA protein in human VSMC.

INDUSTRIAL APPLICABILITY

The ribozyme of the present invention can specifically cleave PDGF-A chain mRNA thereby reducing the expression of PDGF-AA protein, and thus it can be a gene therapeutic agent for vascular proliferative diseases such as hypertension, coronary restenosis after PTCA, and the like.

Sequence list free text
  SEQ ID NO: 1

Artificial sequence: Description of synthetic RNA

A base sequence of ribozyme
  SEQ ID NO: 2

A base sequence targeted by ribozyme
  SEQ ID NO: 3

Artificial sequence: Description of synthetic DNA

A base sequence of a sense primer containing the GUC cleavage site
  SEQ ID NO: 4

Artificial sequence: Description of synthetic DNA

A base sequence of an antisense primer containing the GUC cleavage site
  SEQ ID NO: 5

Artificial sequence: Description of synthetic DNA

A base sequence of a sense primer to human 18S ribosome RNA
  SEQ ID NO: 6

Artificial sequence: Description of synthetic DNA

A base sequence of an antisense primer to human 18S ribosome RNA
  SEQ ID NO: 7

Artificial sequence: Description of synthetic DNA

A base sequence of an antisense ODN
  SEQ ID NO: 8

Artificial sequence: Description of synthetic DNA

A base sequence of a nonsense ODN
  SEQ ID NO: 9

Artificial sequence: Description of synthetic DNA-RNA chimera

A base sequence of a hammerhead-type ribozyme
  SEQ ID NO: 10

Artificial sequence: Description of synthetic DNA-RNA chimera

A base sequence of a mismatch ribozyme
  SEQ ID NO: 11

Artificial sequence: Description of synthetic RNA

A base sequence of a target RNA
  SEQ ID NO: 12

Artificial sequence: Description of synthetic RNA

A base sequence of an unmodified ribozyme
  SEQ ID NO: 13

Artificial sequence: Description of synthetic RNA

A base sequence of a mismatch ribozyme
  SEQ ID NO: 14

A base sequence of ribozyme: n contains at least two nucleotides capable of forming a complementary base pair, and three nucleotides capable of forming a loop.

---

The invention claimed is:

1. A ribozyme comprising the following nucleotide sequence (I'): 5'-GUGGCAUGCUGAUGANNNNNG AAACCCCGUG-3' (I') (SEQ ID NO:16) wherein A, C, G and U represent a ribonucleotide whose base component is adenine, cytosine, guanine and uracil, respectively, wherein the sequence of NNNNN contains at least two nucleotides capable of forming a complementary base pair with each other and three nucleotides capable of forming a loop.

2. A complex of the ribozyme of claim 1 with a liposome.

3. A method of preparing the ribozyme of claim 1 by chemical synthesis which comprises:
synthesizing said ribozyme with T7 RNA polymerase from a synthetic DNA template containing a 17-base promoter region followed by a 38-base complement of the ribozyme sequence.

4. A pharmaceutical composition comprising as an active ingredient the ribozyme of claim 1 or the complex of claim 2.

5. The ribozyme of claim 1, which is a chimera of DNA and RNA.

6. The ribozyme of claim 1 comprising the following nucleotide sequence (II'): 5'-GUGGCAUGCUGAUG AGUCCUUGCGGACGAAACCCCGUG-3'(II') (SEQ ID NO: 1).

7. A method for treating vascular proliferative diseases comprising:
administering an effective amount of the pharmaceutical composition of claim 4 to a patient in need thereof.

8. The method of claim 6, wherein said vascular proliferative diseases are selected from the group consisting of hypertension and restenosis.

9. A method of specifically cleaving a target RNA, which comprises
annealing the ribozyme of claim 1 to said target RNA in a reaction mixture, heating and then cooling the reaction mixture, and then adding $MgCl_2$ to the annealed ribozyme and the target RNA in a buffer to initiate cleavage.

10. The method of claim 9, in which the target RNA is human platelet-derived growth factor (PDGF)-A chain mRNA.

11. The method of claim 9 or 10, wherein the target RNA comprises the following nucleotide sequence: 5'-CACGGG GUCCAUGCCAC-3' (SEQ ID NO:2) wherein A, C, G and U represent a ribonucleotide whose base component is adenine, cytosine, guanine and uracil, respectively.

* * * * *

UNITED STATES PATENT AND TRADEMARK OFFICE
CERTIFICATE OF CORRECTION

PATENT NO. : 7,078,390 B1
APPLICATION NO. : 10/110274
DATED : July 18, 2006
INVENTOR(S) : Noboru Fukuda It is certified that error appears in the above-identified patent and that said Letters Patent is hereby corrected as shown below:

On The Title Page: Item (54)

Please amend the title as follows:

"RIBOZYMES TO GROWTH FACTOR ORIGINATING IN HUMAN PLATELET"

--RIBOZYME TO HUMAN PLATELET-DERIVED GROWTH FACTOR--

Signed and Sealed this

Seventeenth Day of April, 2007

JON W. DUDAS
*Director of the United States Patent and Trademark Office*

UNITED STATES PATENT AND TRADEMARK OFFICE
CERTIFICATE OF CORRECTION

PATENT NO.         : 7,078,390 B1
APPLICATION NO. : 10/110274
DATED              : July 18, 2006
INVENTOR(S)        : Noboru Fukuda Page 1 of 1

It is certified that error appears in the above-identified patent and that said Letters Patent is hereby corrected as shown below:

On the Title Page: Item (54)
In the Title:

Please amend the title as follows:

delete "RIBOZYMES TO GROWTH FACTOR ORIGINATING IN HUMAN PLATELET"

insert --RIBOZYME TO HUMAN PLATELET-DERIVED GROWTH FACTOR--

Signed and Sealed this

Fifteenth Day of May, 2007

JON W. DUDAS
*Director of the United States Patent and Trademark Office*

SEQUENCE LISTING

<160> NUMBER OF SEQ ID NOS: 16

<210> SEQ ID NO 1
<211> LENGTH: 38
<212> TYPE: RNA
<213> ORGANISM: Artificial Sequence
<220> FEATURE:
<223> OTHER INFORMATION: synthetic RNA base sequence of a ribozyme

<400> SEQUENCE: 1
guggcaugcu gaugaguccu ugcggacgaa accccgug                    38

<210> SEQ ID NO 2
<211> LENGTH: 17
<212> TYPE: RNA
<213> ORGANISM: Homo sapiens
<220> FEATURE:

```
<221> NAME/KEY: misc_feature
<222> LOCATION: (1)..(17)
<223> OTHER INFORMATION: base sequence of a target for a ribozyme

<400> SEQUENCE: 2
cacggggucc augccac                                                   17

<210> SEQ ID NO 3
<211> LENGTH: 20
<212> TYPE: DNA
<213> ORGANISM: Artificial Sequence
<220> FEATURE:
<223> OTHER INFORMATION: synthetic DNA base sequence of a sense primer
      containing GUC cleavage site; directed to Homo sapiens

<400> SEQUENCE: 3
gcagtcagat ccacagcatc                                                20

<210> SEQ ID NO 4
<211> LENGTH: 20
<212> TYPE: DNA
<213> ORGANISM: Artificial Sequence
<220> FEATURE:
<223> OTHER INFORMATION: synthetic DNA base sequence of an antisense
      primer containing GUC cleavage site; directed to Homo sapiens

<400> SEQUENCE: 4
tcctctaacc tcacctggac                                                20

<210> SEQ ID NO 5
<211> LENGTH: 20
<212> TYPE: DNA
<213> ORGANISM: Artificial Sequence
<220> FEATURE:
<223> OTHER INFORMATION: synthetic DNA base sequence of a sense primer
      for human 18S ribosome RNA

<400> SEQUENCE: 5
tcaagaacga aagtcggagg                                                20

<210> SEQ ID NO 6
<211> LENGTH: 20
<212> TYPE: DNA
<213> ORGANISM: Artificial Sequence
<220> FEATURE:
<223> OTHER INFORMATION: synthetic DNA base sequence of an antisense
      primer for human 18S ribosome RNA

<400> SEQUENCE: 6
ggacatctaa gggcatcaca                                                20

<210> SEQ ID NO 7
<211> LENGTH: 15
<212> TYPE: DNA
<213> ORGANISM: Artificial Sequence
<220> FEATURE:
<223> OTHER INFORMATION: synthetic DNA base sequence of an antisense ODN

<400> SEQUENCE: 7
aggtcctcat cgcgt                                                     15

<210> SEQ ID NO 8
<211> LENGTH: 15
<212> TYPE: DNA
<213> ORGANISM: Artificial Sequence
<220> FEATURE:
<223> OTHER INFORMATION: synthetic DNA base sequence of a non-sense ODN
```

-continued

```
<400> SEQUENCE: 8
tgccgtcagc tgcta                                                    15

<210> SEQ ID NO 9
<211> LENGTH: 38
<212> TYPE: DNA
<213> ORGANISM: Artificial Sequence
<220> FEATURE:
<223> OTHER INFORMATION: synthetic DNA-RNA chimera base sequence of a
      hammerhead ribozyme

<400> SEQUENCE: 9
cggtggtgcu gaugagtcct tgcggacgaa acccttga                            38

<210> SEQ ID NO 10
<211> LENGTH: 38
<212> TYPE: DNA
<213> ORGANISM: Artificial Sequence
<220> FEATURE:
<223> OTHER INFORMATION: synthetic DNA-RNA chimera base sequence of a
      mismatch ribozyme

<400> SEQUENCE: 10
cggtggtgcu gaugagtcct tgcggacgaa ccccttga                            38

<210> SEQ ID NO 11
<211> LENGTH: 85
<212> TYPE: RNA
<213> ORGANISM: Artificial Sequence
<220> FEATURE:
<223> OTHER INFORMATION: synthetic RNA base sequence of a target RNA

<400> SEQUENCE: 11
cgucaagugc cagcccucaa ggguccacca ccgcaguguc aagguggcca aaguggagua    60
ugucaggaag aagccaaaau ugaaa                                          85

<210> SEQ ID NO 12
<211> LENGTH: 38
<212> TYPE: RNA
<213> ORGANISM: Artificial Sequence
<220> FEATURE:
<223> OTHER INFORMATION: synthetic RNA base sequence of an unmodified
      ribozyme

<400> SEQUENCE: 12
cgguggugcu gaugaguccu ugcggacgaa acccuuga                            38

<210> SEQ ID NO 13
<211> LENGTH: 38
<212> TYPE: RNA
<213> ORGANISM: Artificial Sequence
<220> FEATURE:
<223> OTHER INFORMATION: synthetic RNA base sequence of a mismatch
      ribozyme

<400> SEQUENCE: 13
guggcaugcu gaugaguccu ugcggacgaa cccccgug                            38

<210> SEQ ID NO 14
<211> LENGTH: 31
<212> TYPE: RNA
<213> ORGANISM: Artificial Sequence
<220> FEATURE:
<223> OTHER INFORMATION: base sequence of a ribozyme
<220> FEATURE:
```

```
<221> NAME/KEY: stem_loop
<222> LOCATION: (16)..(20)
<223> OTHER INFORMATION: N1 = position 16 "N". N2 = positions 17-19
      "N". N3 = position 20 "N". N1 and N3 comprises at least two
      nucleotides capable of forming a complementary base pair and N2 is
      at least three nucleotides capable of forming a loop.
<220> FEATURE:
<221> NAME/KEY: misc_feature
<222> LOCATION: (16)..(20)
<223> OTHER INFORMATION: N1 = position 16 "N". N2 = positions 17-19
      "N". N3 = position 20 "N". N1 and N3 comprises at least two
      nucleotides capable of forming a complementary base pair and N2 is
      at least three nucleotides capable of forming a loop.

<400> SEQUENCE: 14
guggcaugcu gaugannnnn gaaacccgu g                              31

<210> SEQ ID NO 15
<211> LENGTH: 200
<212> TYPE: DNA
<213> ORGANISM: Homo sapiens

<400> SEQUENCE: 15
ccacagcauc cgggaccucc agcgacuccu ggagauagac uccguaggga gugaggauuc    60
uuuggacacc agccugagag cucacggggu ccaugccacu aagcaugugc ccgagaagcg   120
gccccugccc auucggagga agagaagcau cgaggaagcu gucccgcug ucugcaagac    180 caggacgguc auuuacgaga                                              200

<210> SEQ ID NO 16
<211> LENGTH: 31
<212> TYPE: RNA
<213> ORGANISM: Artificial Sequence
<220> FEATURE:
<223> OTHER INFORMATION: base sequence of a ribozyme
<220> FEATURE:
<221> NAME/KEY: misc_feature
<222> LOCATION: (16)..(20)
<223> OTHER INFORMATION: nnnnn contains at least two nucleotides capable
      of forming a complementary base pair with each other and three
      nucleotides capable of forming a loop.

<400> SEQUENCE: 16
guggcaugcu gaugannnnn gaaacccgu g                              31
```